United States Patent [19]

Leeson et al.

[11] Patent Number: 5,614,518
[45] Date of Patent: Mar. 25, 1997

[54] MORPHOLINE DERIVATIVES AS DOPAMINE RECEPTOR SUBTYPE LIGANDS

[75] Inventors: Paul D. Leeson, Monmouth Junction, N.J.; Graham A. Showell, Welwyn Garden City, United Kingdom

[73] Assignee: Merck Sharp & Dohme Ltd., Hoddesdon, United Kingdom

[21] Appl. No.: 647,926
[22] PCT Filed: Nov. 21, 1994
[86] PCT No.: PCT/GB94/02557
  § 371 Date: May 20, 1996
  § 102(e) Date: May 20, 1996
[87] PCT Pub. No.: WO95/14690
  PCT Pub. Date: Jun. 1, 1995
[51] Int. Cl.$^6$ .................. A61K 31/535; C07D 413/06
[52] U.S. Cl. ..................... 514/234.5; 514/235.2; 544/127; 544/128; 544/139; 544/140; 544/143; 544/144
[58] Field of Search .................. 544/127, 128, 544/143, 139; 514/234.5

[56] References Cited

FOREIGN PATENT DOCUMENTS 1550656  4/1976  United Kingdom.

*Primary Examiner*—Robert W. Ramsner
*Attorney, Agent, or Firm*—Robert J. North; Melvin Winokur

[57] ABSTRACT

A class of substituted morpholine derivatives of formula

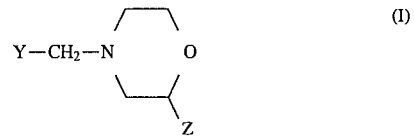

wherein

Y represents an optionally substituted bicyclic heteroaromatic ring system containing one or two nitrogen atoms, the ring system comprising a six-membered aromatic or heteroaromatic ring fused to a five- or six-membered heteroaromatic ring; and Z represents an optionally substituted arylalkyl, aryloxymethyl or arylalkoxymethyl group, are ligands for dopamine receptor subtypes within the body and are therefore useful in the treatment and/or prevention of disorders of the dopamine system, in particular schizophrenia.

9 Claims, No Drawings

MORPHOLINE DERIVATIVES AS DOPAMINE RECEPTOR SUBTYPE LIGANDS

This application is a 371 of PCT/GB94/02557 filed Nov. 21, 1994.

This invention relates to a particular class of morpholine derivatives which are ligands for dopamine receptor subtypes within the body and are therefore of use in the treatment and/or prevention of disorders of the dopamine system, including schizophrenia, depression, nausea, Parkinson's disease, tardive dyskinesias and extrapyramidal side-effects associated with treatment by conventional neuroleptic agents, neuroleptic malignant syndrome, and disorders of hypothalamic-pituitary function such as hyperprolactinaemia and amenorrhoea.

Upper gastrointestinal tract motility is believed to be under the control of the dopamine system. The compounds according to the present invention may thus be of use in the prevention and/or treatment of gastrointestinal disorders, and the facilitation of gastric emptying.

Dependence-inducing agents such as cocaine and amphetamine have been shown to interact with the dopamine system. Compounds capable of counteracting this effect, including the compounds in accordance with the present invention, may accordingly be of value in the prevention or reduction of dependence on a dependence-inducing agent.

Dopamine is known to be a peripheral vasodilator; for example, it has been shown to exert a dilatory effect on the renal vascular bed. This implies that the compounds of the present invention may be beneficial in controlling vascular blood flow.

The localisation of dopamine receptor mRNA in rat heart and large vessels has been noted. This suggests a role for dopamine receptor ligands in controlling cardiovascular function, either by affecting cardiac and smooth muscle contractility or by modulating the secretion of vasoactive substances. The compounds according to the present invention may thereforel be of assistance in the prevention and/or treatment of such conditions as hypertension and congestive heart failure.

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., *Nature* (London), 1991, 350, 610) and $D_5$ (Sunahara et al., *Nature* (London), 1991, 350, 614) receptor subtypes have been described.

The compounds in accordance with the present invention, being ligands for dopamine receptor subtypes within the body, are accordingly of use in the treatment and/or prevention of disorders of the dopamine system.

The present invention accordingly provides a compound of formula I, or a salt thereof or a prodrug thereof:

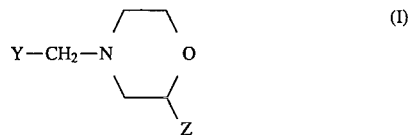

(I)

wherein
Y represents an optionally substituted bicyclic heteroaromatic ring system containing one or two nitrogen atoms, the ring system comprising a six-membered aromatic or heteroaromatic ring fused to a five- or six-membered heteroaromatic ring; and Z represents an optionally substituted aryl($C_{1-6}$)alkyl, aryloxymethyl or aryl($C_{1-6}$)alkoxymethyl group.

The bicyclic heteroaromatic ring system Y in formula I above comprises a phenyl or pyridyl moiety fused at any position to a pyrrolyl or pyridyl moiety; or a phenyl moiety fused at any position to a pyrazolyl, imidazolyl, pyrazinyl, pyrimidinyl or pyridazinyl moiety. Suitably, the ring system Y comprises a phenyl or pyridyl moiety fused at any position to a pyrrolyl, pyridyl or imidazolyl moiety. More particularly, Y may represent an optionally substituted 2- or 3-indolyl, 2- or 3-quinolyl, 3-indazolyl, 2-benzimidazolyl, or 2- or 3-pyrrolo[2,3-b]pyridyl ring system.

The aryl moiety of the substituent Z in formula I above is suitably an optionally substituted phenyl or naphthyl group.

As used herein, the expression "$C_{1-6}$ alkyl", and derived expressions such as "$C_{1-6}$ alkoxy", refers to straight-chained and branched groups containing from 1 to 6 carbon atoms. Typical examples of alkyl groups include methyl and ethyl groups, and straight-chained or branched propyl and butyl groups. Particular alkyl groups include methyl, ethyl, n-propyl, isopropyl, n-butyl and t-butyl.

The groups Y and Z as defined above may each be unsubstituted, or independently substituted by one or more, preferably up to three, optional substituents. Examples of suitable substituents on the groups Y and Z include halogen, trifluoromethyl, cyano, nitro, amino, $C_{1-6}$ alkylamino, di($C_{1-6}$)alkylamino, $C_{1-6}$ alkyl, $C_{1-6}$ alkoxy, aryl($C_{1-6}$) alkoxy and $C_{2-6}$ alkylcarbonyl.

The term "halogen" as used herein includes fluorine, chlorine, bromine and iodine, especially chlorine.

Particular values for the group Z as defined above include benzyl, phenethyl, phenoxymethyl, chlorophenoxymethyl, methoxy-phenoxymethyl and benzyloxymethyl.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

The compounds according to the invention have at least one asymmetric centre, and they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

A particular sub-class of compounds according to the invention is represented by the compounds of formula IIA, and salts and prodrugs thereof:

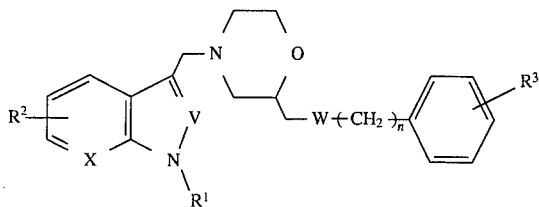

wherein n is zero, 1 or 2;

one of V and X is CH or nitrogen and the other is CH;

W represents a chemical bond or an oxygen atom;

$R^1$ represents hydrogen or $C_{1-6}$ alkyl; and $R^2$ and $R^3$ independently represent hydrogen, halogen, trifluoromethyl, cyano, nitro, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl.

Suitably, one of V and X represents nitrogen and the other is CH.

Suitably, $R^1$ is hydrogen.

Suitable values of $R^2$ include hydrogen, methyl, ethyl, isopropyl, methoxy, benzyloxy, fluoro and chloro, especially hydrogen.

Suitably, $R^3$ represents hydrogen, chloro or methoxy, especially chloro.

Another sub-class of compounds according to the invention is represented by the compounds of formula IIB, and salts and prodrugs thereof:

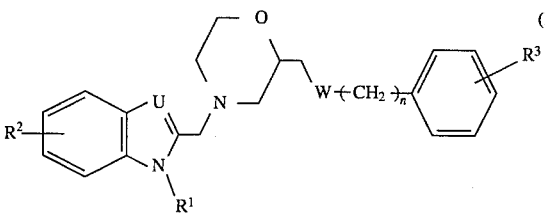

wherein n, W, $R^1$, $R^2$ and $R^3$ are as defined with reference to formula IIA above; and U represents nitrogen or CH.

A further sub-class of compounds according to the invention is represented by the compounds of formula IIC, and salts and prodrugs thereof:

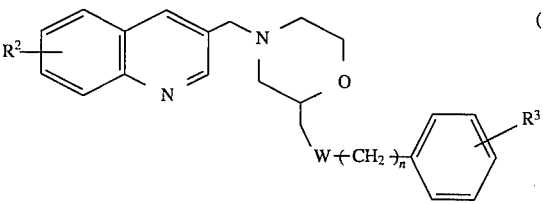

wherein n, W, $R^2$ and $R^3$ are as defined with reference to formula IIA above.

Specific compounds within the scope of the present invention include:

3-(2-benzylmorpholin-4-ylmethyl)indole;
3-(2-phenoxymethylmorpholin-4-ylmethyl)indole;
3-[2-(2-phenylethyl)morpholin-4-ylmethyl]indole;
3-(2-phenoxymethylmorpholin-4-ylmethyl)-1H-pyrrolo[2,3-b]pyridine;
3-[2-(2-phenylethyl)morpholin-4-ylmethyl]-1H-pyrrolo[2,3-b]pyridine;
2-(2-phenoxymethylmorpholin-4-ylmethyl)benzimidazole;
2-[2-(2-phenylethyl)morpholin-4-ylmethyl)benzimidazole;
3-[2-(4-chlorophenoxymethyl)morpholin-4-ylmethyl]-1H-pyrrolo[2,3-b]pyridine;
2-[2-(4-chlorophenoxymethyl)morpholin-4-ylmethyl]benzimidazole;
3-(2-phenoxymethylmorpholin-4-ylmethyl)quinoline;
3-[2(S)-(benzyloxymethyl)morpholin-4-ylmethyl]-1H-pyrrolo[2,3-b]pyridine;
3-[2(R)-(benzyloxymethyl)morpholin-4-ylmethyl]-1H-pyrrolo[2,3-b]pyridine;
3-[2-(4-methoxyphenoxymethyl)morpholin-4-ylmethyl]-1H-pyrrolo[2,3-b]pyridine;
3-[2-(3-chlorophenoxymethyl)morpholin-4-ylmethyl]-1H-pyrrolo[2,3-b]pyridine; and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a compound of formula IV:

$$Y-CH_2-L \quad (III)$$

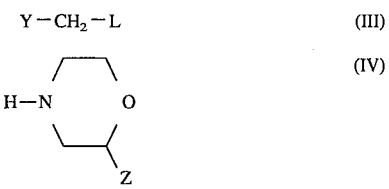

(IV)

wherein Y and Z are as defined above, and L represents a suitable leaving group.

The leaving group L is suitably a halogen atom, e.g. chloro; or a dialkylamino group, e.g. dimethylamino.

When L represents a halogen atom, the reaction between compounds III and IV is conveniently carried out by stirring the reactants at an elevated temperature under basic conditions in a suitable solvent, for example potassium carbonate in ethanol at a temperature in the region of 80° C. Where L represents a dialkylamino group, the reaction is conveniently effected by heating the reactants in an inert solvent such as toluene, typically at the reflux temperature of the solvent.

In an alternative procedure, the compounds according to the invention wherein Y represents an optionally substituted indol-3-yl, indazol-3-yl or 4-, 5-, 6- or 7-azaindol-3-yl moiety may be prepared by reacting a compound of formula IV as defined above with a compound of formula V:

$$Y^1-H \quad (V)$$

wherein $Y^1$ represents an optionally substituted indol-3-yl, indazol-3-yl or 4-, 5-, 6- or 7-azaindol-3-yl moiety; in the presence of a substantially equimolar amount of formaldehyde.

The reaction is conveniently carried out by stirring the reactants at ambient temperature in aqueous acetic acid, optionally in the presence of a buffer such as sodium acetate trihydrate.

The formaldehyde may be utilised in the form of paraformaldehyde; or as a solution of formaldehyde in an inert solvent, e.g. 38% aqueous formaldehyde.

In a further procedure, the compounds according to the invention wherein Y represents an optionally substituted 3-quinolyl moiety may be prepared by reacting a compound of formula IV as defined above with a compound of formula VI:

$$Y^2-CHO \quad (VI)$$

wherein $Y^2$ represents an optionally substituted 3-quinolyl moiety; in the presence of anhydrous formic acid.

The reaction is conveniently effected by stirring the reactants at an elevated temperature, typically a temperature in the region of 120° C. This is an example of the Leuckart-Wallach reaction, which is described in more detail in *Org. React.*, 1949, 5, 301.

The intermediates of formula IV may conveniently be prepared by reacting ethanolamine-O-sulphate with the appropriate epoxide of formula VII:

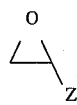

(VII)

wherein Z is as defined above; as described in *J. Pharm. Pharmacol.*, 1990, 42, 797.

The reaction is suitably effected by stirring the reactants with sodium hydroxide in aqueous methanol at a temperature in the region of 40° C.; followed by treating the reaction mixture with solid sodium hydroxide and heating in toluene to approximately 65° C.

Where they are not commercially available, the starting materials of formula III, V, VI and VII may be prepared by procedures analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds useful in this invention potently inhibit [$^3$H]-spiperone binding to human dopamine $D_4$ receptor subtypes expressed in clonal cell lines.

[$^3$H]-Spiperone Binding Studies

Clonal cell lines expressing the human dopamine $D_4$ receptor subtype were harvested in PBS and then lysed in 10 mM Tris-HCl pH 7.4 buffer containing 5 mM $MgSO_4$ for 20 min on ice. Membranes were centrifuged at 50,000 g for 15 min at 4° C. and the resulting pellets resuspended in assay buffer (50 mM Tris-HCl pH 7.4 containing 5 mM EDTA, 1.5 mM $CaCl_2$, 5 mM $MgCl_2$, 5 mM KCl, 120 mM NaCl, and 0.1% ascorbic acid) at 20 mg/ml wet weight. Incubations were carried out for 60 min at room temperature (22° C.) in the presence of 0.05–2 nM [$^3$H]-spiperone or 0.2 nM for displacement studies and were initiated by addition of 20–100 μg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 µM apomorphine and radioactivity determined by counting in a LKB beta counter. Binding parameters were determined by non-linear least squares regression analysis, from which the inhibition constant $K_i$ could be calculated for each test compound.

The compounds of the accompanying Examples were tested in the above assay, and all were found to possess a $K_i$ value for displacement of [$^3$H]-spiperone from the human dopamine $D_4$ receptor subtype of below 1.5 µM.

EXAMPLE 1

3-((2(RS)-(Phenylmethyl)morpholin-4-yl)methyl)-indole Hydrogen Oxalate 3-(Dimethylaminomethyl)indole (688 mg, 3.9 mmol) and 2(RS)-(phenylmethyl)morpholine (700 mg, 3.9 mmol, *J. Pharm. Pharmacol.* 1990, 42, 797–799), were heated at reflux in toluene (20 ml), with stirring, for 16 hours. The reaction mixture was cooled, evaporated to dryness and the crude product was purified by column chromatography on silica using ethyl acetate/methanol (9:1) to afford the title product free base as a beige gum (1.10 g, 92%). The hydrogen oxalate salt had mp 122°–124° C. (ethanol). $^1$H NMR (360 MHz, D$_2$O) δ2.84 (2H, d, J=6 Hz), 2.96 (1H, dd, $J_1$=$J_2$=12 Hz), 3.16 (1H, ddd, $J_1$=4, $J_2$=$J_3$=12 Hz), 3.40–3.47 (2H, m), 3.74 (1H, dd, $J_1$=$J_2$=12 Hz), 3.97–4.10 (2H, m), 4.51 (1H, d, J=14Hz), 4.58 (1H, d, J=14 Hz), 7.20–7.36 (7H, m), 7.55–7.58 (2H, m), 7.71 (1H, d, J=7 Hz). Found: C, 66.31; H, 6.01; N, 7.01. $C_{20}H_{22}N_2O$. $C_2H_2O_4$ requires C, 66.65; H, 6.10; N, 7.07%.

EXAMPLE 2

3-((2(RS)-(Phenoxymethhyl)morpholin-4-yl)methyl)-indole Hydrogen Oxalate

Step A: 2(RS)-(Phenoxymethyl)morpholine

2-Aminoethyl hydrogen sulphate (49 g, 0.347 mol) was added in portions to a mixture of (±)-1,2-epoxy-3-phenoxypropane (11.2 ml, 0.083 mol), sodium hydroxide (26.4 g, 0.66 mol) in water (50 ml) and methanol (20 ml). After addition the reaction mixture was stirred at 40° C. (oil bath temperature) for 2 hours. The reaction mixture was cooled, sodium hydroxide pellets (20.65 g, 0.516 mol) and toluene (80 ml) were added, then the reaction mixture stirred, whilst heating at 65° C. (oil bath temperature) for 7.5 hours. The reaction mixture was cooled, toluene (40 ml) and water (140 ml) were added. The toluene phase was extracted with 2M hydrochloric acid (2×60 ml). The acid extracts were combined, 40% sodium hydroxide solution added to pH=11, then extracted with toluene (2×60 ml). The combined organics were dried (sodium sulphate) then evaporated to give a colourless gum (10 g) which was purified by column chromatography on silica, using neat ethyl acetate to remove the lipophilic impurities then ethyl acetate/methanol/ammonia (9:1:0.1) to elute the required product as a colourless oil (7.0 g, 44%). Rf 0.22 in dichloromethane/methanol (9:1) on silica plates MS CI$^+$, m/z=194 for (M+H)$^+$. $^1$H NMR (360 MHz, CDCl$_3$) δ2.54–2.85 (2H, m), 2.92 (1H, ddd, $J_1$=2, $J_2$=$J_3$=12 Hz), 3.05 (1H, dd, $J_1$=2, $J_2$=12 Hz), 3.67 (1H, ddd, $J_1$=2, $J_2$=J3=12 Hz), 3.83–4.03 (4H, m), 6.88–6.97 (3H, m), 7.23–7.30 (2H, m).

Step B: 3-((2(RS)-(Phenoxymethyl)morpholin-4-yl)methyl)-indole Hydrogen Oxalate 3-(Dimethylaminomethyl)indole (688 mg, 3.9 mmol) and 2(RS)-(phenoxymethyl)morpholine (754 mg, 3.9 mmol) were heated at reflux in toluene (20 ml), with stirring, for 5 hours. The reaction mixture was cooled, treated with silica (200 mg) and activated charcoal (200 mg), then filtered and evaporated to afford the title compound free base (1.15 g, 91%) as a gum. The hydrogen oxalate salt had m.p 169°–°171° C. (ethanol/acetone). $^1$H NMR (360 MHz, DMSO-d$_6$) δ2.40–2.60 (1H, m), 3.01 (1H, d, J=12 Hz), 3.17 (1H, d, J=12 Hz), 3.62 (1H, dd, $J_1$=$J_2$=12 Hz), 3.90–4.05 (7H, m), 6.88–7.41 (9H, m), 7.70 (1H, d, J=8 Hz), 11.19 (1H, broad s). Found: C, 66.94; H, 6.15; N, 7.12. $C_{20}H_{22}N_2O_2$. 0.7$C_2H_2O_4$ requires C, 66.69; H, 6.12; N, 7.27%.

EXAMPLE 3

3-((2(RS)-(2-Phenylethyl)morpholin-4-yl)methyl)-indole Hydrogen Oxalate

Step A: (+)-(3,4-Epoxybutyl)-benzene

Dimethyl sulphoxide (100 ml) was added over 5 minutes to sodium hydride (6.76 g of a 55% oil dispersion, 0.155 mol) under a nitrogen atmosphere. The mixture was stirred vigorously for 10 minutes, then diluted with anhydrous tetrahydrofuran (80 ml). The mixture was cooled to 5° C. and a solution of trimethylsulphonium iodide (31.63 g, 0.155 mol) in dimethyl sulphoxide (80 ml) was added slowly keeping the temperature of the reaction mixture at 5° C. After addition the reaction mixture was stirred at 5° C. for 2 minutes then a solution of hydrocinnamaldehyde (20.0 g, 0.149 mol) in anhydrous tetrahydrofuran (20 ml) was added over 1 minute. After 15 minutes at 5° C. the cooling bath was removed and the reaction mixture was stirred at room temperature for 2 hours. The reaction mixture was quenched with water (200 ml), then extracted with ethyl acetate (3×100 ml). The combined extracts were washed with saturated sodium chloride solution (200 ml), dried (potassium carbonate) then evaporated to give an orange oil which was purified by distillation under vacuum. (±)-(3,4-Epoxybutyl)-benzene was obtained as a colourless oil (5.2 g, 23%), bp 80°–85° C. (4 mbar).

Step B: 2(RS)-(2-Phenylethyl)morpholine

The title compound was obtained (2.55 g, 38%) from (±)-(3,4-epoxybutyl)-benzene (5.15 g, 0.0348 mol) and 2-aminoethyl hydrogen sulphate (20.63 g, 0.146 mol) as described in Example 2, Step A MS, CI$^+$, m/z=192 for (M+H)$^+$. $^1$H NMR (360 MHz, CDCl$_3$) δ1.63–1.85 (2H, m), 2.53–2.91 (6H, m), 3.38–3.42 (1H, m), 3.58 (1H, ddd, $J_1$=3, $J_2$=$J_3$=11 Hz), 3.88 (1H, dd, $J_1$=2, $J_2$=11 Hz), 7.15–7.29 (5H, m).

Step C: 3-((2(RS)-(2-Phenylethyl)morpholin-4-yl)methyl)-indole Hydrogen Oxalate

The title compound free base was obtained (0.94 g) from 3-(Dimethylaminomethyl)indole and 2(RS)-(2-phenylethyl)morpholine as described in Example 2, Step B. The hydrogen oxalate salt had mp 170°–171° C. (ethanol). $^1$H NMR (360 MHz, DMDO-d$_6$) δ1.64–1.70 (2H, m), 2.44–2.69 (4H, m), 3.05–3.16 (2H, m), 3.53–3.60 (2H, m), 3.92 (1H, d, J=12 Hz), 4.14 (2H, s), 7.02–7.28 (7H, m), 7.39–7.42 (2H, m), 7.70 (1H, d, J=8 Hz), 11.29 (1H, s). Found: C, 68.04; H, 6.44; N, 6.98. $C_{21}H_{24}N_2O.0.9C_2H_2O_4$ requires C, 68.21; H, 6.48; N, 6.98%.

EXAMPLE 4

3-((2(RS)-(Phenoxymethyl)morpholin-4-yl)methyl)-1H-pyrrolo[2,3-b]pyridine Hydrogen Oxalate 38% Aqueous formaldehyde (0.9 ml) was added dropwise to a stirred solution of 2(RS)-(phenoxymethyl)morpholine (2.10 g, 0.0109 mmol) in glacial acetic acid (8 ml) and water (4 ml). After stirring for 10 minutes this solution was treated with 1H-pyrrolo[2,3-b]pyridine (1.18 g, 0.010 mmol). The reaction mixture was stirred at room temperature for 20 hours. The mixture was poured onto 2M sodium hydroxide solution (180 ml) and extracted with ethyl acetate (3×80 ml). The combined extracts were washed with saturated sodium chloride solution (80 ml), dried (sodium sulphate) then evaporated to give a gum which was purified by column chromatography on silica (300 g) using ethyl acetate/methanol (20:1) to afford the title compound free base (2.30 g, 65%) as a gum. The hydrogen oxalate salt had mp 188°–189° C. (ethanol) MS, CI$^+$, m/z=324 for (M+H)$^+$. $^1$H NMR (360 MHz, DMSO-d$_6$) δ2.55–2.75 (2H, m), 3.14 and 3.30 (each 2H, each 2H, each d, J=12 Hz), 3.86–4.03 (4H, m), 4.08–4.20 (3H, m), 6.84–7.27 (6H, m), 7.46 (1H, s), 8.07 (1H, dd, J$_1$=1, J$_2$=8 Hz), 8.27 (1H, dd, J$_1$=1, J$_2$=5 Hz), 11.43 (1H, s). Found: C, 60.61; H, 5.43; N, 9.97. C$_{19}$H$_{21}$N$_3$O2.C$_2$H$_2$O$_4$ requires C, 61.01; H, 5.61; N, 10.16%.

EXAMPLE 5

3-((2(RS)-(2-Phenylethyl)morpholin-4-yl)methyl)-1H-pyrrolo[2,3-b]pyridine Hydrogen Oxalate Step A: 3-Dimethylaminomethyl-1H-pyrrolo[2,3-b]pyridine A mixture of 1H-pyrrolo[2,3-b]pyridine (18.07 g, 0.153 mol), dimethylamine hydrochloride (13.11 g, 0.161 mol) and paraformaldehyde (4.92 g, 0.164 mol) in n-butanol (500 ml) was heated at reflux for 35 minutes. The mixture was allowed to cool overnight and the precipitated solid collected by filtration. The filtrate was evaporated and the residue triturated with ethyl acetate to afford a second solid. The solids were combined, suspended in saturated aqueous potassium carbonate solution (500 ml) and extracted with dichloromethane (twice). The combined extracts were washed with saturated potassium carbonate (250 ml) then saturated sodium chloride solution (500 ml), dried (magnesium sulphate) then evaporated to a small volume, with the product crystallising out of solution during evaporation. Diethyl ether was added and the title compound collected as a solid (18.13 g, 67%). $^1$H NMR (360 MHz, DMSO-d$_6$) δ2.19 (6H, s), 3.61 (2H, s), 7.03 (1H, dd, J$_1$=5, J$_2$=8 Hz), 7.36 (1H, d, J=2 Hz), 8.00 (1H, dd, J$_1$=2, J$_2$=8 Hz), 8.20 (1H, dd, J$_1$=2, J$_2$=5 Hz), 11.47 (1H, broad s).

Step B: 3-((2(RS)-(2-Phenylethyl)morpholin-4-yl)methyl)-1H-pyrrolo[2,3-b]pyridine Hydrogen Oxalate 3-Dimethylaminomethyl-1H-pyrrolo[2,3-b]pyridine (400 mg, 2.28 mmol) and 2(RS)-(2-phenylethyl)morpholine (437 mg, 2.28 mmol) were heated at reflux in toluene (20 ml), with stirring, for 20 hours. The reaction mixture was cooled, treated with silica (200 mg) and activated charcoal (200 mg), filtered, then evaporated to dryness to give the title compound free base as a colourless gum (570 mg, 78%). The hydrogen oxalate salt had mp 200°–201° C. (ethanol/water). MS, CI$^+$, m/z 322 for (M+H)$^+$. $^1$H NMR (360 MHz, DMSO-d$_6$) δ1.64–1.71 (2H, m), 2.47–2.70 (4H, m), 3.02–3.14 (2H, m), 3.43–3.59 (2H, m), 3.93 (1H, d, J=10 Hz), 4.13 (2H, s), 7.10–7.28 (6H, m), 7.55 (1H, s), 8.12 (1H, d, J=7 Hz), 8.25 (1H, dd, J$_1$=1, J$_2$=5 Hz), 11.83 (1H, s). Found: C, 64.07; H, 5.98; N, 10.02. C$_{20}$H$_{23}$N$_3$O.C$_2$H$_2$O$_4$ requires C, 64.22; H, 6.12; N, 10.21%.

EXAMPLE 6

2-((2(RS)-(Phenoxymethyl)morpholin-4-yl)methyl)benzimidazole 2-(Chloromethyl)benzimidazole (172 mg, 1.03 mmol) and 2(RS)-(phenoxymethyl)morpholine (200 mg) were heated in ethanol (8 ml) at 80° C. (oil bath temperature) in the presence of potassium carbonate (142 mg, 1.03 mmol) for 2 hours. The mixture was cooled then evaporated to dryness. The residue was partitioned between water (10 ml) and ethyl acetate (25 ml). The organic layer was separated and the aqueous re-extracted with ethyl acetate (25 ml). The combined organics were dried (sodium sulphate) then evaporated to give a beige gum which was purified by column chromatography on silica (150 g) using ethyl acetate to ethyl acetate/methanol (25:1) to afford the title compound as a pale yellow solid (220 mg, 66%). mp 171°–172° C. (ethyl acetate/n-hexane). MS, CI$^+$, mz=324 for (M+H)$^+$. $^1$H NMR (360 MHz, CDCl$_3$) δ2.40 (1H, dd, J$_1$=J$_2$=10 Hz), 2.51 (1H, ddd, J$_1$=3, J$_2$=J$_3$=10 Hz), 2.79 (1H, d, J=10 Hz), 2.99 (1H, d, J=10 Hz), 3.82 (1H, ddd, J$_1$=3, J$_2$=J$_3$=10 Hz), 3.91–4.06 (6H, m), 6.88 (2H, dd, J$_1$=1, J$_2$=8 Hz), 6.95 (1H, ddd, J$_1$=1, J$_2$=J$_3$=8 Hz), 7.24–7.29 (4H, m), 7.57–7.61 (2H, m). Found: C, 70.55; H, 6.51; N, 12.96. C$_{19}$H$_{21}$N$_3$O$_2$ requires C, 70.57; H, 6.55; N, 12.99%.

EXAMPLE 7

2-((2(RS)-(2-Phenylethyl)morpholin-4-yl)methyl)benzimidazole Hydrogen Oxalate

The title compound free base was obtained (220 mg, 52%) from 2-(chloromethyl)benzimidazole, 2(RS)-(2-phenylethyl)morpholine and potassium carbonate as described in Example 6. The hydrogen oxalate salt had mp 197°–198° C. (ethanol/water) MS, CI$^+$, m/z=322 for (M+H)$^+$. $^1$H NMR (360 MHz, DMSO-d$_6$) δ1.62–1.70 (2H, m), 2.07 (1H, dd, J$_1$=J$_2$=11 Hz), 2.32 (1H, ddd, J$_1$=3, J$_2$=J$_3$=11 Hz), 2.55–2.69 (2H, m), 2.77 (1H, d, J =11 Hz), 2.84 (1H, d, J =11 Hz), 3.41–3.45 (1H, m), 3.55 (1H, dd, J$_1$=J$_2$=11 Hz), 3.81–3.85 (3H, m), 7.13–7.27 (7H, m), 7.51–7.54 (2H, m). Found: C, 60.24; H, 5.40; N, 9.03. C$_{20}$H$_{23}$N$_3$O.1.5C$_2$H$_2$O$_4$ requires C, 60.52; H, 5.74; N, 9.21%.

EXAMPLE 8

3-((2(RS)-(4-Chlorophenoxymethyl)morpholin-4-yl)methyl)-1H-pyrrolo[2,3-b]pyridine Hydrogen Oxalate Step A: 2(RS)-(4-Chlorophenoxymethyl)morpholine The title compound was obtained (10.8 g, 36%) from (±)-4-chlorophenyl-2,3-epoxypropyl ether and 2-aminoethyl hydrogen sulphate as described in Example 2, Step A. mp 51°–52° C. MS, CI$^+$, m/z=228 for (M+H)$^+$. $^1$H NMR (360 MHz, CDCl$_3$) δ2.71–3.04 (4H, m), 3.67 (1H, ddd, J$_1$=3, J$_2$=J$_3$=11 Hz), 3.82–3.98 (4H, m), 6.84 (2H, d, J=8 Hz), 7.21 (2H, d, J=8 Hz). Found: C, 57.92; H, 5.94; N, 5.92. C$_{11}$H$_{14}$ClNO$_2$ requires C, 58.03; H, 6.20; N, 6.15%.

Step B: 3-((2(RS)-(4-Chlorophenoxymethyl)morpholin-4-yl)methyl)-1H-pyrrolo-[2,3-b]pyridine Hydrogen Oxalate 2(RS)-(4-Chlorophenoxymethyl)morpholine (650 mg, 2.85 mmol) and 3-dimethylaminomethyl-1H-pyrrolo[2,3-b] pyridine (500 mg, 2.85 mmol) were heated at reflux in toluene (20 ml), with stirring, for 18 hours. The reaction mixture was cooled, treated with silica (200 mg) and activated charcoal (200 mg), filtered, then evaporated to give the title compound free base as a flaky solid (870 mg, 85%), mp 140°–141° C. The hydrogen oxalate salt had mp 190°–191° C. (ethanol/water) MS, CI$^+$, m/z=358 for (M+H)$^+$. $^1$H NMR (360 MHz, DMSO-d$_6$) δ2.50–2.68 (2H, m), 3.04 (1H, d, J=12 Hz), 3.18 (1H, d, J=12 Hz), 3.64 (1H, dd, J$_1$=J$_2$=12 Hz), 3.90–4.02 (4H, m), 4.11 (2H, s), 6.94 (2H, d, J=9 Hz), 7.11 (1H, dd, J$_1$=4, J$_2$=8 Hz), 7.31 (2H, d, J=9 Hz), 7.54 (1H, s), 8.12 (1H, dd, $J_1$=1, $J_2$=8 Hz), 8.24 (1H, dd, $J_1$=1, $J_2$=4 Hz), ].1.76 (1H, s). Found: C, 56.57; H, 4.77; N, 9.18. $C_{19}H_{20}ClN_3O_2 \cdot C_2H_2O_4$ requires C, 56.32; H, 4.95; N, 9.38%.

EXAMPLE 9

2-((2(RS)-(4-Chlorophenoxymethyl)morpholin-4-yl)methylbenzimidazole

The title compound was obtained (300 mg, 56%) from 2(RS)-(4-Chlorophenoxymethyl)morpholine and 2-(chloromethyl)benzimidazole as described in Example 6. mp 163°–164° C. (ethyl acetate/n-hexane). Found: C, 64.04; H, 5.54; N, 11.55. $C_{19}H_{20}ClN_3O_2$ requires C, 63.77; H, 5.63; N, 11.74%.

EXAMPLE 10

3-((2(RS)-(Phenoxymethyl)morpholin-4-yl)methyl)-quinoline Hydrogen Oxalate

Quinoline-3-carboxaldehyde (447 mg, 2.8 mmol), 2(RS)-(phenoxymethyl)morpholine (500 mg, 2.59 mmol) and anhydrous formic acid (0.1 ml) were heated at 120° C. (oil bath temperature), with stirring, for 6 hours. The reaction mixture was cooled, 2M hydrochloric acid (20 ml) added and the solution washed with ethyl acetate (20 ml). The aqueous was basified to pH=11 with 2M aqueous sodium hydroxide, then extracted with ethyl acetate (2×30 ml). The combined organics were dried (sodium sulphate) then evaporated to give a gum which was purified by column chromatography on silica (200 g) using ethyl acetate to ethyl acetate/methanol (25:1) to afford the title compound free base as a pale yellow gum (340 mg, 36%). The hydrogen oxalate salt had mp 164°–166° C. (ethanol/water). MS CI$^+$, m/z=335 for (M+H)$^+$. $^1$H NMR (360 MHz, DMSO-$d_6$) δ2.23 (1H, dd, $J_1$=$J_2$=11 Hz), 2.35 (1H, ddd, $J_1$=3, $J_2$=$J_3$=11 Hz), 2.80 (1H, d, J=11 Hz), 2.97 (1H, d, J=11 Hz), 3.61 (1H, ddd, $J_1$=2, $J_2$=$J_3$=11 Hz), 3.80–3.92 (4H, m), 3.96 (2H, d, J=5 Hz), 6.89–6.94 (3H, m), 7.23–7.28 (2H, m), 7.59–7.64 (1H, m), 7.73–7.78 (1H, m), 7.97–8.04 (2H, m), 8.29 (1H, d, J=2 Hz), 8.90 (1H, d, J=2 Hz). Found: C, 63.38; H, 5.84; N, 6.48. $C_{21}H_{22}N_2O_2 \cdot C_2H_2O_4 \cdot 0.5H_2O$ requires C, 63.73; H, 5.81; N, 6.46%.

EXAMPLE 11

3-((2(S)-(Phenylmethlyloxymethyl)morpholin-4-yl)methyl)-1H-pyrrolo[2,3-b]pyridine Hydrogen Oxalate Step A: (+)-2(S)-(Phenylmethyloxymethyl)morpholine The title compound was obtained (2.33 g, 23%) from 2-aminoethyl hydrogen sulphate and (−)-2(benzyloxymethyl)oxirane as described in Example 2, Step A. $^1$H NMR (360 MHz, CDCl$_3$) δ2.65 (1H, dd, $J_1$=10, $J_2$=12 Hz), 2.78–2.93 (3H, m), 3.41 (1H, dd, $J_1$=5, $J_2$=10 Hz), 3.48 (1H, dd, $J_1$=5, $J_2$=10 Hz), 3.58–3.68 (2H, m), 3.89 (1H, d, J=10 Hz), 4.54 (1H, d, J=12 Hz), 4.56 (1H, d, J=12 Hz), 7.25–7.34 (5H, m), [α]$^{27°}$ $^C{}_D$+2.4° (c=1.0, methanol), MS, CI$^+$, m/z= 208 for (M+H)$^+$.

Step B: 3-((2(S)-(Phenylmethyloxymethyl)morpholin-4-yl)methyl)-1H-pyrrolo[2,3-b]pyridine Hydrogen Oxalate The title compound free base was obtained (670 mg, 87%) from (+)-2(S)-(phenylmethyloxymethyl)morpholine and 3-dimethylaminomethyl-1H-pyrrolo[2,3-b]pyridine as described in Example 8, Step B. The hydrogen oxalate salt had mp 160°–161° C. (ethanol/water) MS, CI$^+$, m/z=338 for (M+H)$^+$. $^1$H NMR (360 MHz, DMSO-$d_6$) δ2.58 (1H, dd, $J_1$=$J_2$=11 Hz), 2.72 (1H, dd, $J_1$=$J_2$=11 Hz), 3.10 (1H, d, J=11 Hz), 3.19 (1H, d, J=11 Hz), 3.43 (1H, dd, $J_1$=4, $J_2$=10 Hz), 3.48 (1H, dd, $J_1$=4, $J_2$=10 Hz), 3.63 (1H, dd, $J_1$=$J_2$=11 Hz), 3.75–3.78 (1H, m), 3.92 (1H, d, J=11 Hz), 4.21 (2H, s), 4.45 (2H, s), 7.13 (1H, dd, $J_1$=4.5, $J_2$=8 Hz), 7.24–7.36 (5H, m), 7.57 (1H, s), 8.16 (1H, dd, $J_1$=1, $J_2$=8 Hz), 8.26 (1H, dd, $J_1$=1, $J_2$=4.5 Hz), 11.84 (1H, s). [α]$^{26°}$ $^C{}_D$=−14.0° (c=0.5, methanol/water (14:1)). Found: C, 59.39; H, 5.46; N, 9.23. $C_{20}H_{23}N_3O_2 \cdot 1.3C_2H_2O_4$ requires C, 59.73; H, 5.68; N, 9.25%.

EXAMPLE 12

3-((2(R)-(Phenylmethyloxymethyl)morpholin-4-yl)methyl)-1H-pyrrolo[2,3-b]pyridine Hydrogen Oxalate Step A: (−)-2(R)-(Phenylmethyloxymethyl)morpholine The title compound was obtained (2.85 g, 32%) from 2-aminomethyl hydrogen sulphate and (+)-2(benzyloxymethyl)oxirane as described in Example 2, Step A. MS, CI$^+$, m/z=208 for (M+H)$^+$. [α]$^{27°}$ $^C{}_D$=−2.0° (c=1.0, methanol).

Step B: 3-((2(R)-(Phenylmethyloxymethyl)morpholin-4-yl)methyl)-1H-pyrrolo[2,3-b]pyridine Hydrogen Oxalate The title compound free base was obtained (620 mg, 81%) from (−)-2(R)-(phenylmethyloxymethyl)morpholine and 3-dimethylaminomethyl-1H-pyrrolo[2,3-b]pyridine as described in Example 8, Step B. The hydrogen oxalate salt had mp 160°–161° C. (ethanol/water) MS, CI$^+$, m/z=338 for (M+H)$^+$. [α]$^{26°}$ $^C{}_D$+136° (c=0.5, methanol/water (14:1). Found: C, 60.04; H, 5.67; N, 9.26. $C_{20}H_{23}N_3O_2 \cdot 1.2C_2H_2O_4$ requires C, 60.40; H, 5.75; N, 9 43%.

EXAMPLE 13

3-((2(RS)-(4-Methoxyphenoxymethyl)morpholin-4-yl)methyl)-1H-pyrrolo[2,3-b]pyridine Hydrogen Oxalate Step A: 2(RS)-(4-Methoxyphenoxymethyl)morpholine The title compound was obtained (10.66 g, 35%) from (±)-2,3-epoxypropyl-4-methoxyphenyl ether and 2-aminoethyl hydrogen sulphate as described in Example 2, Step A. mp 34°–35° C. MS, CI$^+$, m/z=224 for (M+H)$^+$, $^1$H NMR (360 MHz, CDCl$_3$) δ2.71–3.10 (4H, m), 3.67 (1H, ddd, $J_1$=3, $J_2$=$J_3$=11 Hz), 3.76 (3H, s), 3.80–4.00 (4H, m), 6.81 (2H, d, J=7 Hz), 6.85 (2H, d, J=7 Hz). Found: C, 62.24; H, 7.61; N, 6.23. $C_{12}H_{17}NO_3 \cdot 0.5H_2O$ requires C, 62.05; H, 7.81; N, 6.03%.

Step B: ((2(RS)-(4-Methoxyphenoxymethyl)morpholin-4-yl)methyl-1H-pyrrolo[2,3-b]pyridine Hydrogen Oxalate The title compound free base was obtained (710 mg, 70%) from 2(RS)-(4-methoxyphenoxy)methyl)morpholine and 3-dimethylaminomethyl-1H-pyrrolo[2,3-b]pyridine as described in Example 8, Step B. The hydrogen oxalate salt had mp 183°–184° C. (ethanol/water). MS, CI$^+$, m/z=354 for (M+H)$^+$. $^1$H NMR (360 MHz, DMSO-$d_6$) δ2.49–2.75 (2H, m), 3.05 (1H, d, J=12 Hz), 3.21 (1H, d, J=12 Hz), 3.64 (1H, dd $J_1$=$J_2$=12 Hz), 3.69 (3H, s), 3.85–4.00 (4H, m), 4.13 (2H, s), 6.84 (4H, s), 7.11 (1H, dd, $J_1$=5, $J_2$=8 Hz), 7.55 (1H, s), 8.13 (1H, dd, $J_1$=1, $J_2$=8 Hz), 8.24 (1H, dd, $J_1$=1, $J_2$=5 Hz), 11.79 (1H, s). Found: C, 59.42; H, 5.69; N, 9.23. $C_{20}H_{23}N_3O_3 \cdot C_{20}H_{23}O_4$ requires C, 59.59; H, 5.68; N, 9.47%.

EXAMPLE 14

((2(RS)-(3-Chlorophenoxymethyl)morpholin-4-yl)methyl)-1H-pyrrolo[2,3-b]pyridine Hydrogen Oxalate Step A: 2(RS)-(3-Chlorophenoxymethyl)morpholine The title compound was obtained (9.8 g, 32%) as a gum from (±)-3-chlorophenyl-2,3-epoxypropyl ether and 2-aminoethyl hydrogen sulphate as described in Example 2, Step A. MS, CI$^+$, m/z=228 for (M+H)$^+$. $^1$H NMR (360 MHz, CDCl$_3$) δ2.72–3.05 (4H, m), 3.68 (1H, ddd, J$_1$=3, J$_2$=J$_3$=11 Hz), 3.82–4.00 (4H, m), 6.78–6.82 (1H, m), 6.90–6.95 (2H, m), 7.18 (1H, dd, J$_1$=J$_2$=8 Hz). Found: C, 57.53; H, 6.21; N, 5.75. C$_{11}$H$_{14}$ClNO$_2$ requires C, 58.03; H, 6.20; N, 6.15%.

Step B: ((2(RS)-(3-Chlorophenoxymethyl)morpholin-4-yl)methyl)-1H-pyrrolo[2,3-b]pyridine Hydrogen Oxalate The title compound free base was obtained (660 mg, 80%) from 2(RS)-(3-chlorophenoxymethyl)morpholine and 3-dimethylaminomethyl-1H-pyrrolo[2,3-b]pyridine as described in Example 8, Step B. The hydrogen oxalate salt had mp 177°–178° C. (ethanol/water). $^1$H NMR (360 MHz, DMSO-d$_6$) δ2.50–2.68 (2H, m), 3.06 (1H, d, J=12 Hz), 3.20 (1H, d, J=12 Hz), 3.66 (1H, dd, J$_1$=J$_2$=12 Hz), 3.92–4.07 (4H, m), 4.13 (2H, s), 6.88–6.92 (1H, m), 6.98–7.02 (2H, m), 7.11 (1H, dd, J$_1$=4, J$_2$=8 Hz), 7.29 (1H, dd, J$_1$=J$_2$=8 Hz), 7.56 (1H, s), 8.13 (1H, d, J=8 Hz), 8.25 (1H, dd, J$_1$=1, J$_2$=4 Hz), 11.80 (1H, s). Found: C, 55.58; H, 5.21; N, 8.92. C$_{19}$H$_{20}$ClNO$_3$O$_2$·C$_2$H$_2$O$_4$·0.25H$_2$O requires C, 55.76; H, 5.01; N, 9.29%.

We claim:

1. A compound of formula I, or a salt thereof or a prodrug thereof:

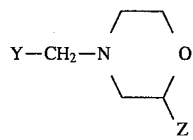

wherein

Y represents an optionally substituted bicyclic heteroaromatic ring system containing one or two nitrogen atoms, the ring system comprising a six-membered aromatic or heteroaromatic ring fused to a five- or six-membered heteroaromatic ring; and Z represents an optionally substituted aryl(C$_{1-6}$)alkyl, aryloxymethyl or aryl(C$_{1-6}$)alkoxymethyl group.

2. A compound as claimed in claim 1 wherein Y represents an optionally substituted 2- or 3-indolyl, 2- or 3-quinolyl, 3-indazolyl, 2-benzimidazolyl, or 2- or 3-pyrrolo[2,3-b]pyridyl ring system.

3. A compound as claimed in claim 1 represented by formula IIA, and salts and prodrugs thereof:

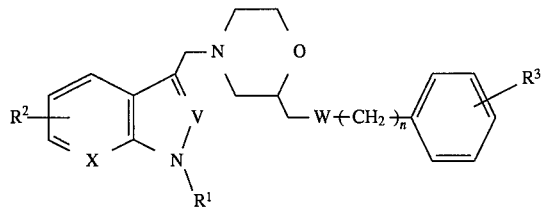

wherein n is zero, 1 or 2;

one of V and X is CH or nitrogen and the other is CH;

W represents a chemical bond or an oxygen atom;

R$^1$ represents hydrogen or C$_{1-6}$ alkyl; and

R$^2$ and R$^3$ independently represent hydrogen, halogen, trifluoromethyl, cyano, nitro, amino, C$_{1-6}$ alkylamino, di(C$_{1-6}$)alkylamino, C$_{1-6}$ alkyl, C$_{1-6}$ alkoxy, aryl(C$_{1-6}$) alkoxy or C$_{2-6}$ alkylcarbonyl.

4. A compound as claimed in claim 1 represented by formula IIB, and salts and prodrugs thereof:

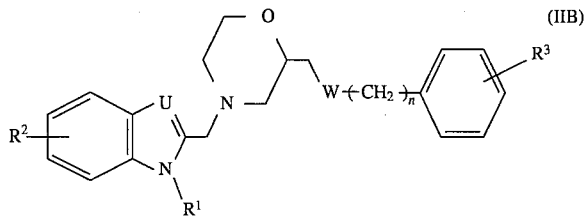

wherein n is zero, 1 or 2;

W represents a chemical bond or an oxygen atom;

R$^1$ represents hydrogen or C$_{1-6}$ alkyl; and

R$^2$ and R$^3$ independently represent hydrogen, halogen, trifluoromethyl, cyano, nitro, amino, C$_{1-6}$ alkylamino, di(C$_{1-6}$)alkylamino, C$_{1-6}$ alkyl, C$_{1-6}$ alkoxy, aryl (C$_{1-6}$) alkoxy, aryl(C$_{1-6}$) alkoxy or C$_{2-6}$ alkylcarbonyl; and U represents nitrogen or CH.

5. A compound as claimed in claim 1 represented by formula IIC, and salts and prodrugs thereof:

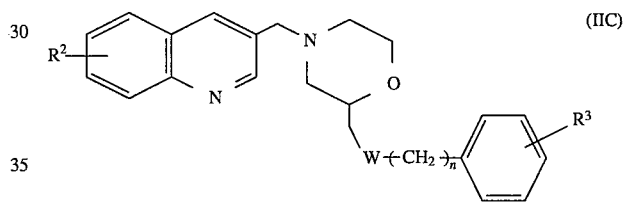

wherein n is zero, 1 or 2;

W represents a chemical bond or an oxygen atom; and

R$^2$ and R$^3$ independently represent hydrogen, halogen, trifluoromethyl, cyano, nitro, amino, C$_{1-6}$ alkylamino, di(C$_{1-6}$)alkylamino, C$_{1-6}$ alkyl, C$_{1-6}$ alkoxy, aryl (C$_{1-6}$) alkoxy, or C$_{2-6}$ alkylcarbonyl.

6. A compound as claimed in claim 1 selected from:
3-(2-benzylmorpholin-4-ylmethyl)indole;
3-(2-phenoxymethylmorpholin-4-ylmethyl)indole;
3-[2-(2-phenylethyl)morpholin-4-ylmethyl]indole;
3-(2-phenoxymethylmorpholin-4-ylmethyl)-1H-pyrrolo[2,3-b]pyridine;
3-[2-(2-phenylethyl)morpholin-4-ylmethyl]-1H-pyrrolo[2,3-b]pyridine;
2-(2-phenoxymethylmorpholin-4-ylmethyl)benzimidazole;
2-[2-(2-phenylethyl)morpholin-4-ylmethyl)benzimidazole;
3-[2-(4-chlorophenoxymethyl)morpholin-4-ylmethyl]-1H-pyrrolo[2,3-b]pyridine;
2-[2-(4-chlorophenoxymethyl)morpholin-4-ylmethyl]benzimidazole;
3-(2-phenoxymethylmorpholin-4-ylmethyl)quinoline;
3-[2(S)-(benzyloxymethyl)morpholin-4-ylmethyl]-1H-pyrrolo[2,3-b]pyridine;
3-[2(R)-(benzyloxymethyl)morpholin-4-ylmethyl]-1H-pyrrolo[2,3-b]pyridine;
3-[2-(4-methoxyphenoxymethyl)morpholin-4-ylmethyl]-1H-pyrrolo[2,3-b]pyridine;
3-[2-(3-chlorophenoxymethyl)morpholin-4-ylmethyl]-1H-pyrrolo[2,3-b]pyridine;

and salts and prodrugs thereof.

7. A pharmaceutical composition comprising a compound as claimed in in claim 1 in association with a pharmaceutically acceptable carrier.

8. A process for the preparation of a compound as claimed in claim 1 which comprises:

(A) reacting a compound of formula III with a compound of formula IV:

$$Y-CH_2-L \quad \text{(III)}$$

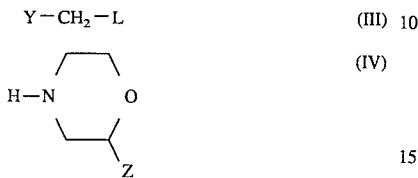

(IV)

wherein Y and Z are as defined in claim 1, and L represents a suitable leaving group; or (B) for the preparation of a compound of formula I wherein Y represents an optionally substituted indol-3-yl, indazol-3-yl or 4-, 5-, 6- or 7-azaindol-3-yl moiety:

reacting a compound of formula IV as defined above with a compound of formula V:

$$Y^1-H \quad \text{(V)}$$

wherein $Y^1$ represents an optionally substituted indol-3-yl, indazol-3-yl or 4-, 5-, 6- or 7-azaindol-3-yl moiety; in the presence of a substantially equimolar amount of formaldehyde; or (C) for the preparation of a compound of formula I wherein Y represents an optionally substituted 3-quinolyl moiety:

reacting a compound of formula IV as defined above with a compound of formula VI:

$$Y^2-CHO \quad \text{(VI)}$$

wherein $Y^2$ represents an optionally substituted 3-quinolyl moiety; in the presence of anhydrous formic acid; and (D) subsequently, where required, converting a compound of formula I initially obtained into a further compound of formula I by conventional methods.

9. A method for the treatment and/or prevention of disorders of the dopamine system, which method comprises administering to a patient in need of such treatment an effective amount of a compound as claimed in claim 1.

* * * * *